(12) United States Patent
Ravi et al.

(10) Patent No.: US 9,682,935 B2
(45) Date of Patent: Jun. 20, 2017

(54) PROCESS FOR PREPARATION OF INDACATEROL OR ITS PHARMACEUTICALLY ACCEPTABLE SALTS

(71) Applicant: Davuluri Ramamohan Rao, Hyderabad (IN)

(72) Inventors: Ponnaiah Ravi, Madurai (IN); Praveen Kumar Neela, Hyderabad (IN); Guruswamy Batthini, Hyderabad (IN); Narayana Venugopalarao, Hyderabad (IN); Naresh Dongari, Nalagonda (IN)

(73) Assignee: Davuluri Ramamohan Rao, Hyderabad (IN)

( * ) Notice: Subject to any disclaimer, the term of this patent is extended or adjusted under 35 U.S.C. 154(b) by 0 days.

(21) Appl. No.: 15/110,410

(22) PCT Filed: Dec. 27, 2014

(86) PCT No.: PCT/IN2014/050006
§ 371 (c)(1),
(2) Date: Jul. 8, 2016

(87) PCT Pub. No.: WO2015/104718
PCT Pub. Date: Jul. 16, 2015

(65) Prior Publication Data
US 2016/0326118 A1 Nov. 10, 2016

(30) Foreign Application Priority Data

Jan. 9, 2014 (IN) .............................. 116/CHE/2014

(51) Int. Cl.
C07D 215/26 (2006.01)
C07F 7/18 (2006.01)

(52) U.S. Cl.
CPC .......... C07D 215/26 (2013.01); C07F 7/1856 (2013.01)

(58) Field of Classification Search
CPC ........................... C07D 215/26; C07F 7/1856
See application file for complete search history.

(56) References Cited

U.S. PATENT DOCUMENTS 9,475,772 B2 * 10/2016 Bonde-Larsen ..... C07D 215/26

FOREIGN PATENT DOCUMENTS

| WO | WO0075114 A1 | 12/2000 |
| WO | 2013132514 | * 9/2013 |
| WO | WO2013132514 A2 | 9/2013 |
| WO | WO2014044288 A1 | 3/2014 |
| WO | 2014/154841 | * 10/2014 |
| WO | WO2014154841 A1 | 10/2014 |

* cited by examiner

Primary Examiner — D M Seaman
(74) Attorney, Agent, or Firm — Ling Wu; Stephen Yang; Ling and Yang Intellectual Property

(57) ABSTRACT

A novel process the for preparation of Indacaterol or its pharmaceutically acceptable salts and novel intermediates employed in the preparation thereof that is economically significant for large scale.

10 Claims, No Drawings

PROCESS FOR PREPARATION OF INDACATEROL OR ITS PHARMACEUTICALLY ACCEPTABLE SALTS

FIELD OF THE INVENTION

The present invention relates to a novel process for preparation of Indacaterol or its pharmaceutically acceptable salts and novel intermediates employed in the preparation thereof.

BACKGROUND OF THE INVENTION

Indacaterol is chemically known as (R)-5-[2-(5,6-Diethylindan-2-ylamino)-1-hydroxyethyl]-8-hydroxy-1H-quinolin-2-one having the formula I as mentioned below:

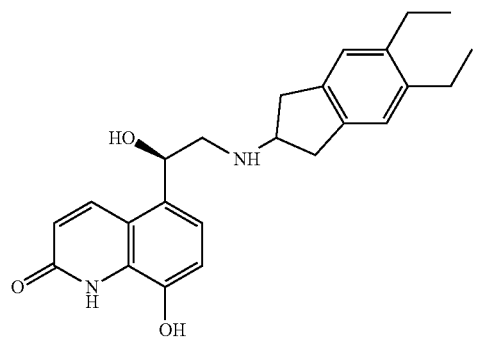

I

Indacaterol is long acting inhaled β2-agonist marketed by Novartis under the trade name Arcapta Neohaler in US and Onbrez in Europe. Indacaterol is marketed as maleate salt. Indacaterol was first disclosed in the U.S. Pat. No. 6,878,721 (herein referred patent US'721). The process for Indacaterol maleate as described in the patent US'721 is depicted below:

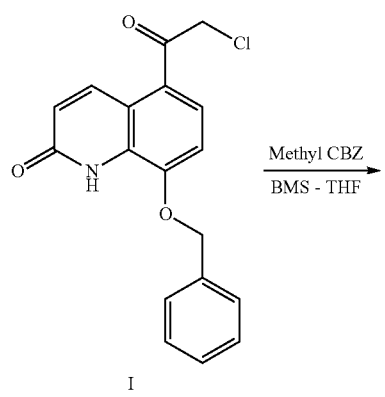

I

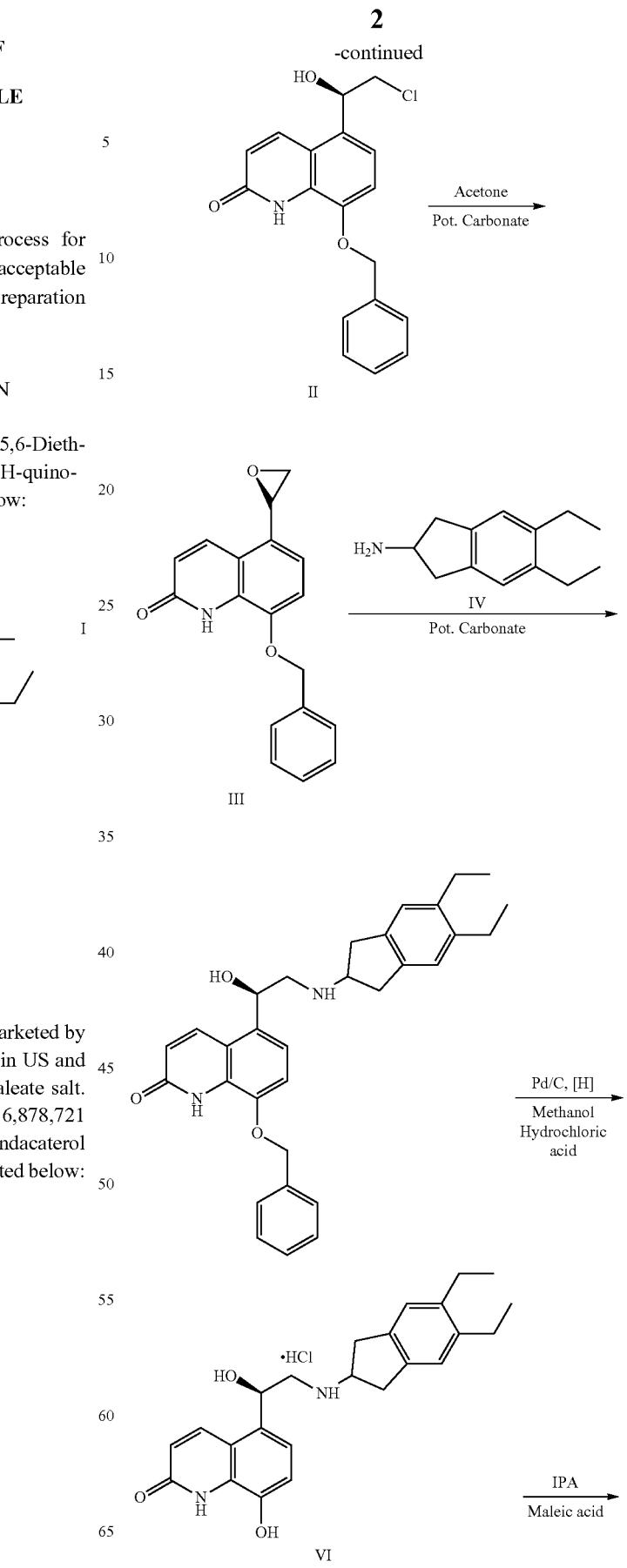

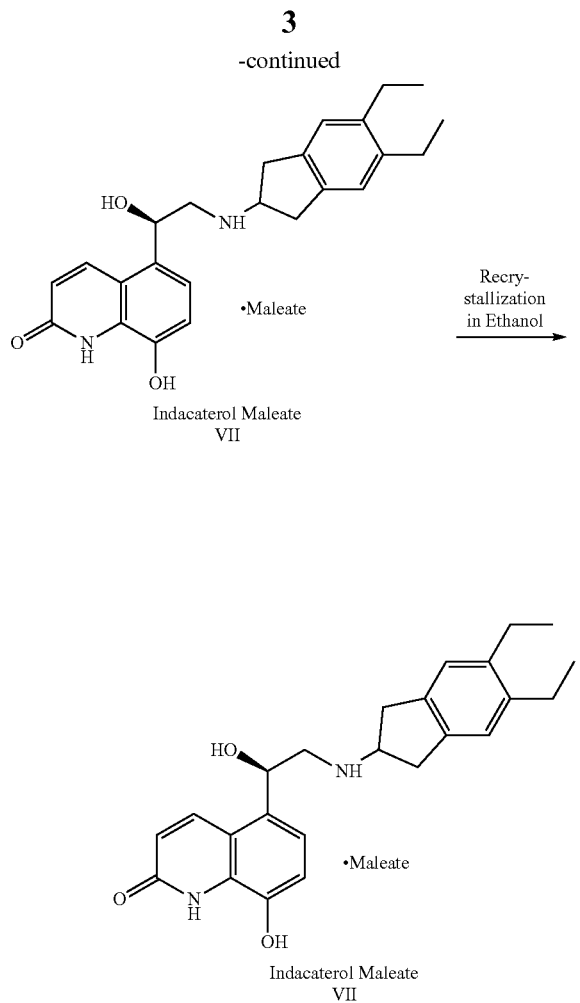

Indacaterol Maleate
VII

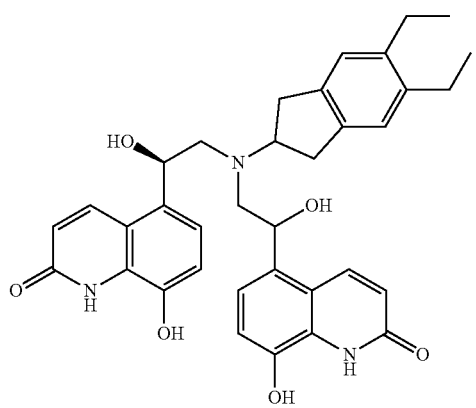

The above process for preparing Indacaterol maleate comprises the step of reacting 8 substituted oxy-5-(R)-oxiranyl-(1H)-quinolin-2-one (III) with 2-amino-(5,6-diethyl)-indan (IV) to form an intermediate 5-[(R)-2-(5,6-diethyl-indan-2-ylamino)-1-hydroxy-ethyl]-8-substituted oxy-(1H)-quinolin-2-one (V). This reaction step is not regioselective, hence along with desired product 5-[(R)-2-(5,6-diethyl-indan-2-ylamino)-1-hydroxy-ethyl]-8-substituted-oxy-(1H)-quinolin-2-one, the below mentioned compounds are also formed as impurities.

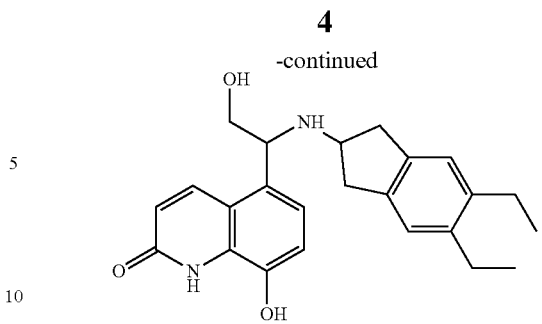

Further, the above reaction mixture contains only about 60% to 80% of desired compound i.e. 5-[(R)-2-(5,6-diethyl-indan-2-ylamino)-1-hydroxy-ethyl]-8-substituted oxy-(1H)-quinolin-2-one. The purification of this intermediate is done using silica gel chromatography which is tedious and requires large amount of solvents and is not suitable for industrial synthesis.

The U.S. Pat. No. 7,534,890 discloses a process that avoids the column purification by the formation of acid addition salts of intermediate (formula-IV). The processes for preparation Indacaterol or its pharmaceutically acceptable salts are also disclosed in WO2000075114, WO20050123684, WO2008093188 and WO2004087668.

It is observed that prior art processes are complicated, costly and not suitable for large scale industrial preparation therefore, there exists a need to develop a novel economically significant process for the preparation of Indacaterol or its pharmaceutically acceptable salts for large scale preparation.

OBJECTS OF THE INVENTION

The primary object of the invention is to provide a novel economically significant process for the preparation of Indacaterol or its pharmaceutically acceptable salts for large scale industrial preparation.

Another object of the invention is to provide novel intermediates for preparation of Indacaterol and process for the preparation thereof.

SUMMARY OF THE INVENTION

Accordingly the invention provides a novel process for the preparation of Indacaterol free base or its pharmaceutically acceptable salt comprising the steps of:
i) treating compound of formula II

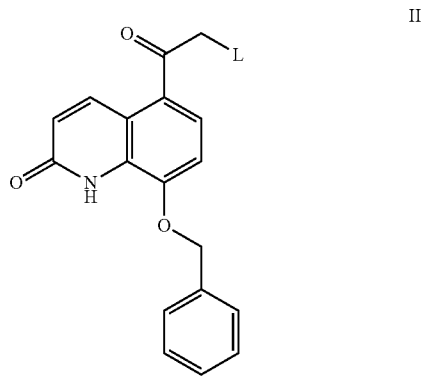

with a reducing agent to obtain compound of formula III

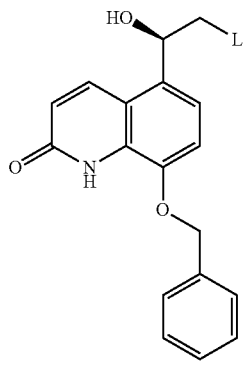

III wherein L is good leaving group;

ii) treating compound of formula III with silylated protecting reagent to obtain compound of formula IV

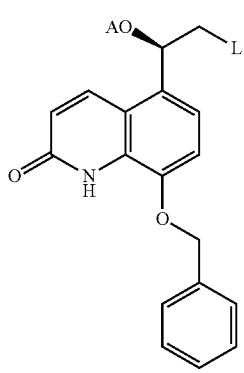

IV wherein A is silylated protective group;

iii) reacting compound of formula IV with compound of formula V or its derivatives in the presence of a base

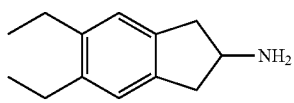

V to obtain compound of formula VI,

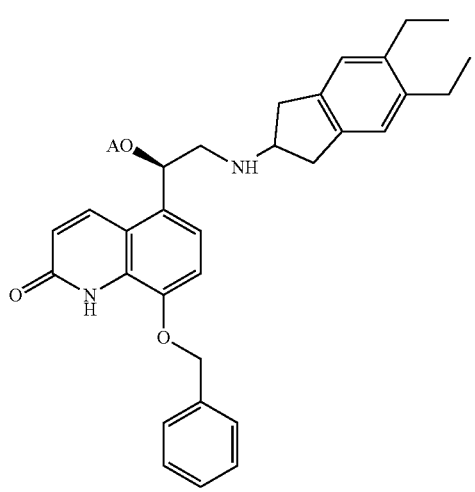

VI iv) desilylating compound of formula VI to obtain compound of formula VII

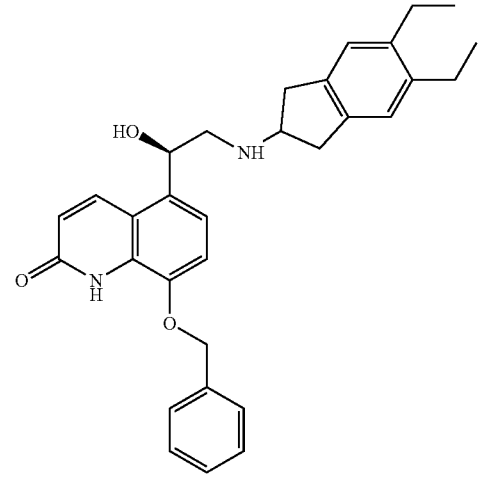

VII v) debenzylating the compound of formula VII to obtain compound of formula I Indacaterol free base;

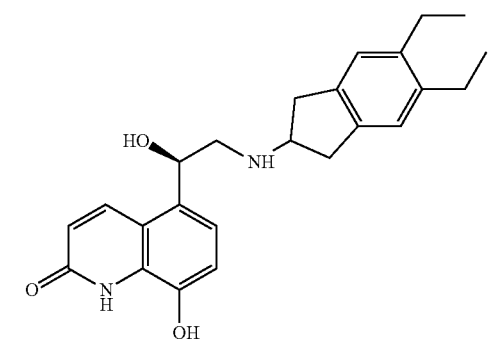

I vi) optionally converting the compound of formula I to its acid addition salts, preferably pharmaceutical acceptable salts.

The invention also provides a process for preparation of compound of formula VI comprising the step of:

i) reacting the compound of formula IV

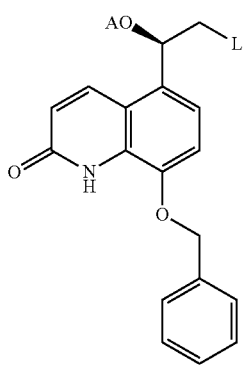

IV with compound of formula V or its derivatives in the presence of a base.

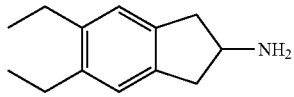

V to obtain compound of formula VI

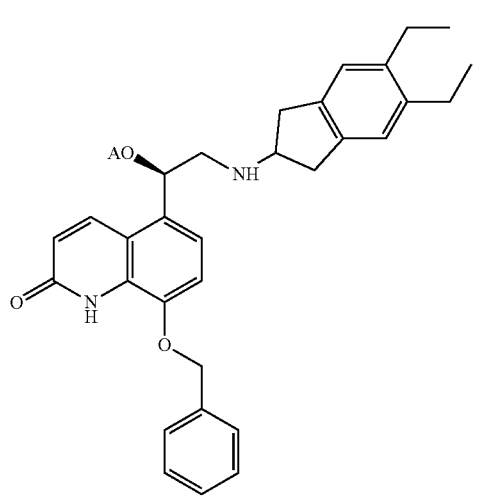

VI wherein A is silylated protective group.

In another embodiment, the invention provides a process for purification of the compound of formula VII (benzyl indacaterol) having below mentioned formula

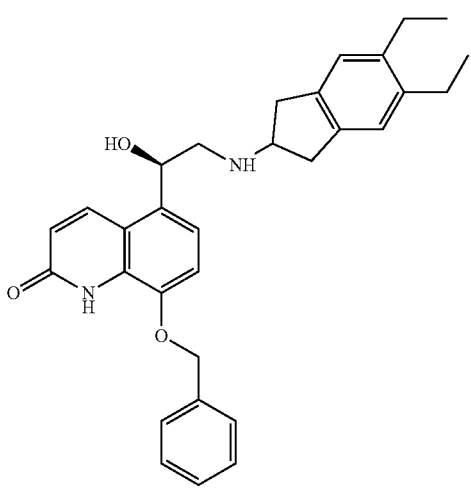

VII comprising the steps of:

(a) treating the compound of formula VII with organic acid salts selected from the group consisting of maleic acid, tartaric acid, mandelic acid, oxalic acid and succinic acid to form organic acid salts of the compound of formula VII; and (b) alkalifying the organic acid salts of the compound of formula VII to obtain compound of formula VII.

In another embodiment, the invention provides compound of formula VI having below mentioned formula

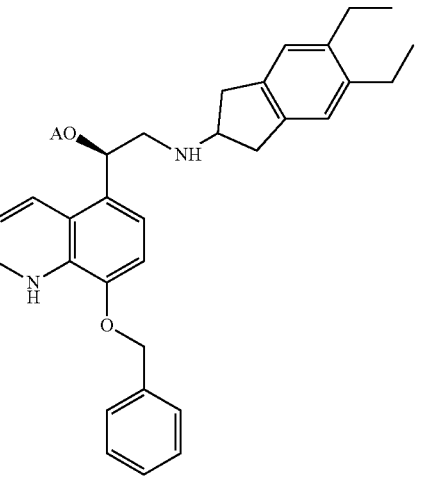

VI wherein A is silylated protective group.

DETAILED DESCRIPTION OF THE INVENTION

The present invention provides an improved process for the preparation of Indacaterol or its pharmaceutically acceptable salts.

In one embodiment, the invention provides a process for preparation of Indacaterol free base or its pharmaceutically acceptable salt comprising the steps of:

i) treating the compound of formula II

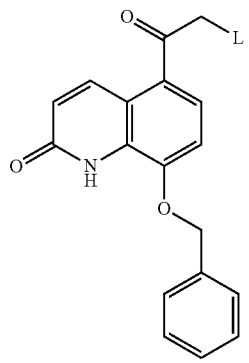

II with the reducing agent to obtain compound of formula III

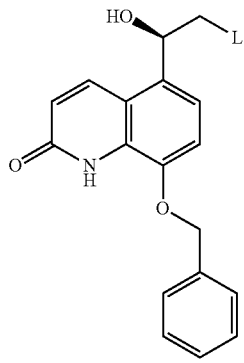

where L is good leaving group;

ii) treating compound of formula III with silylated protecting reagent to obtain compound of formula IV

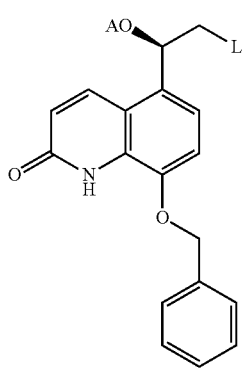

where A is silylated protective group;

iii) reacting compound of formula IV with compound of formula V or its derivatives in the presence of a base

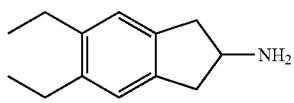

to obtain compound of formula VI,

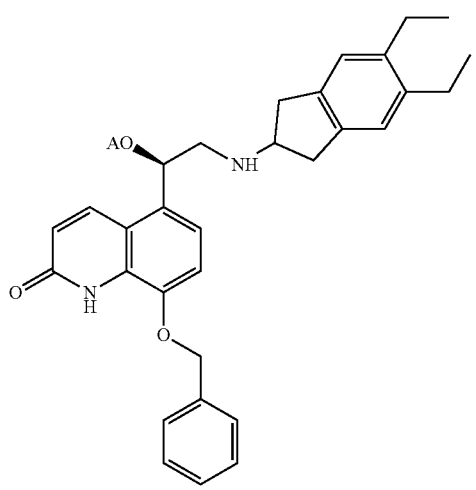

iv) desilylating compound of formula VI to obtain compound of formula VII

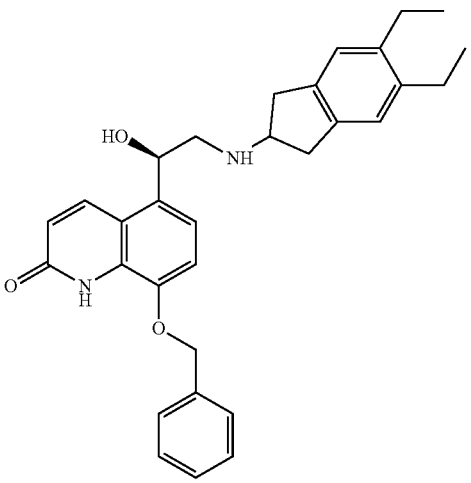

v) debenzylating the compound of formula VII to obtain compound of formula I Indacaterol free base vi) optionally converting the compound of formula I to its acid addition salt, preferably pharmaceutical acceptable salts.

The leaving group represents any suitable leaving group which may be halogen, methoxy, tosylate, mesylate, etc or other known to a person skilled in the art.

The reducing agent employed in step (i) is selected from the group included but not limited to asymmetric reducing agents such as boranes like THF-Borane, DMS-Diborane with chiral catalyst, Methyl CBS, phenyl CBS, DIP chloride, and sodium borohydride, lithium aluminum hydride, alkoxy aluminium hydride, alkoxy borohydrides.

The silylating agent employed in step (ii) may be selected from the group comprising of tert-Butyldimethylsilyl chloride (TBDMSCl), trimethylsilyl chloride, methyldichlorosilane, methyldiethoxysilane, methyldimethoxysilane, trichlorosilane, triethoxysilane, trimethoxysilane, silazane, hexamethyldisilazane, hexamethyldisilizane, chlorotrimethylsilane, bis trimethyl silyl acetamide preferably tert-Butyldimethylsilyl chloride.

The base employed in the step (iii) is selected from the group of organic base or inorganic base, wherein the organic base is selected form the C1 to C6 cyclic or acyclic amines included but not limited to isopropyl amine, diisopropyl amine, diisopropyl ethyl-amine, N-methyl morpholine, N-methyl piperidine, N-methyl piperazine, N-methyl pyridine, N-methyl pyrrolidone, DBU, DABCO, DIPEA and triethylamine. Inorganic base may be selected from the group consisting of alkali metals such as sodium, potassium, lithium or alkali metal carbonates like sodium carbonate, potassium carbonate, cesium carbonate, lithium carbonate or alkali metal bicarbonates like sodium bicarbonate, potassium bicarbonate, lithium bicarbonate, cesium bicarbonate or alkali metal hydroxides like sodium hydroxide, calcium hydroxide, potassium hydroxide, metal alkoxides e.g. alkoxides of sodium, lithium or potassium, sodium tert-butoxide and sodium hydride, including the combination of above organic and inorganic bases in any ratio can be used, preferably N-methyl pyrrolidone.

Desilylation is the reverse of silylation: the silyl group is exchanged for a proton. The desilylating agents employed in the step (iv) is selected from the various fluoride salts such as sodium, potassium, tetra-n-butylammonium fluorides, preferably tetra-n-butylammonium fluoride.

The debenzylating agents employed in step (v) is selected from ceric ammonium nitrate, Sodium bromate with sodium diathionate, Palladium with carbon, Palladium with Aluminium oxide, preferably Palladium with carbon.

The suitable organic solvent employed in step (i) to (vi) is selected from the group but are not limited to alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene and the like and aprotic polar solvents such as dimethyl sulfoxide, N,N-dimethylformamide, N,N-dimethylacetamide and the like; and mixtures thereof.

The second embodiment of the present invention provides a novel process for the preparation of compound of formula VI comprising the step of:

i) reacting compound of formula IV

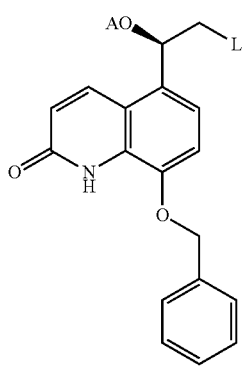

IV with compound of formula V or its derivatives in the presence of a base

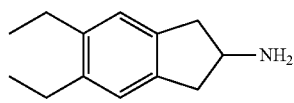

V to obtain compound of formula VI,

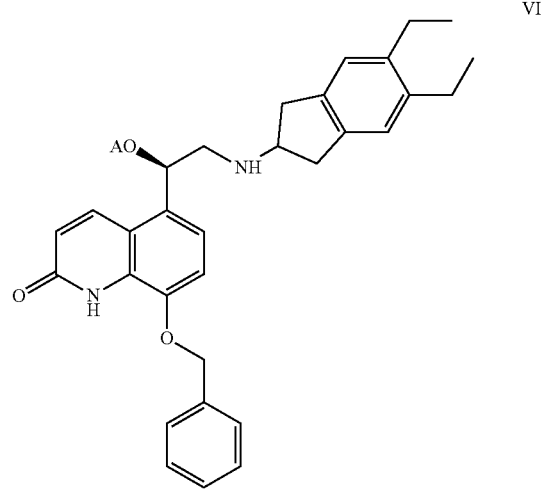 [SMILES: CCc1cc2c(cc1CC)CC(NC[C@H](O)c1ccc(OCc3ccccc3)c3[nH]c(=O)ccc13)C2]

VI where A is silylated protective group.

The leaving group represents any suitable leaving group which may be halogen, methoxy, tosylate, mesylate, etc or other known to a person skilled in the art.

The base employed in the step (i) is selected from the group of organic base or inorganic base, wherein the organic base is selected form the C1 to C6 cyclic or acyclic amines included but not limited to isopropyl amine, diisopropyl amine, diisopropyl ethyl-amine, N-methyl morpholine, N-methyl piperidine, N-methyl piperazine, N-methyl pyridine, DBU, DABCO and triethylamine. Inorganic base may be selected from the group consisting of alkali metals such as sodium, potassium, lithium or alkali metal carbonates like sodium carbonate, potassium carbonate, cesium carbonate, lithium carbonate or alkali metal bicarbonates like sodium bicarbonate, potassium bicarbonate, lithium bicarbonate, cesium bicarbonate or alkali metal hydroxides like sodium hydroxide, calcium hydroxide, potassium hydroxide, metal alkoxides e.g., alkoxides of sodium, lithium or potassium, sodium tert-butoxide and sodium hydride, including the combination of above organic and inorganic bases in any ratio can be used.

The suitable organic solvent employed in step (i) is selected from the group but are not limited to alcohols such as methanol, ethanol, isopropyl alcohol, isobutyl alcohol, tertiary-butyl alcohol and the like; halogenated hydrocarbons such as dichloromethane, ethylene dichloride, chloroform and the like; ketones such as acetone, methyl isobutyl ketone and the like; nitriles such as acetonitrile, propionitrile and the like; ethers such as dimethyl ether, diethyl ether, diisopropyl ether, tetrahydrofuran, methyl tertiary-butyl ether and the like; esters such as ethyl acetate, n-propyl acetate, isopropyl acetate, n-butyl acetate, isobutyl acetate and the like; hydrocarbons such as hexane, benzene, xylene, toluene and the like and aprotic polar solvents such as dimethyl sulfoxide, N,N-dimethylformamide, N,N-dimethylacetamide and the like; and mixtures thereof.

The third embodiment of the present invention provides a process for the purification of the compound of formula VII (benzyl indacaterol) having below mentioned formula

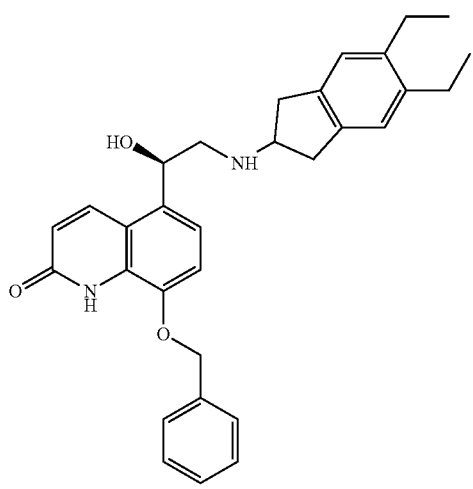

VII comprising the steps of:

(a) treating the compound of formula VII with organic acid salts selected from the group consisting of maleic acid, tartaric acid, mandelic acid, oxalic acid and succinic acid to form organic acid salts of the compound of formula VII; and (b) alkalifying the organic acid salts of the compound of formula VII to obtain compound of formula VII.

The fourth embodiment of the present invention provides a compound of formula VI having below mentioned formula

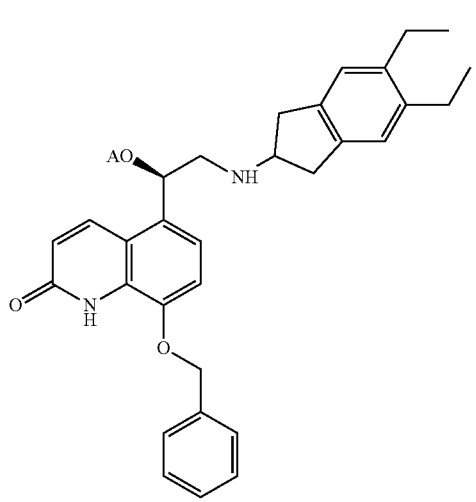

VI wherein A is silylated protective group.

The process of the present invention provides pure Indacaterol maleate having purity not less than 98% preferably more than 99.5% purity is obtained.

The following examples are provided to enable one skilled in the art to practice the invention and are merely illustrative of the process of the invention. However, it is not intended in any way to limit the scope of the present invention.

EXAMPLE

Example 1: Preparation of Compound of Formula III, where L is Bromo

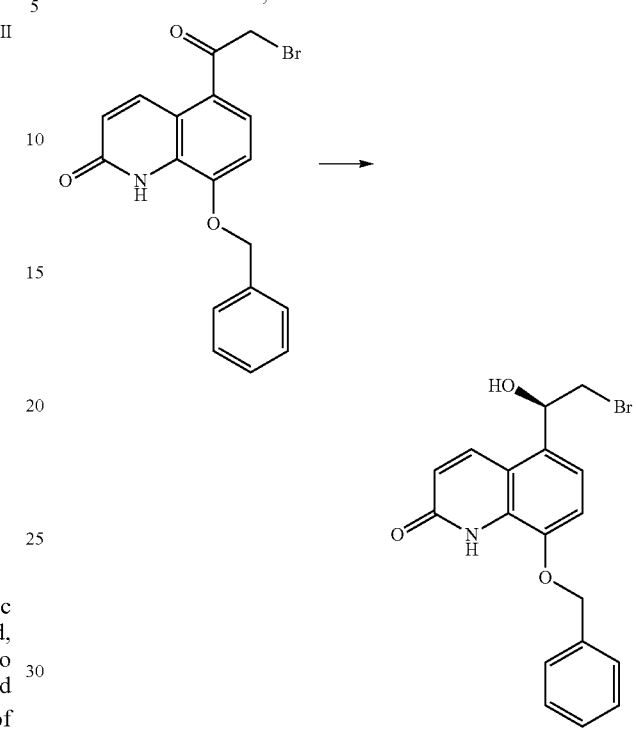

To a mixture of tetrahydrofuran (1400 ml) and Bromo compound (100 g), R-methyl CBS (7.5 g) was slowly added at 25-30° C. under nitrogen atmosphere and cooled to 0-5° C., followed by the addition of Boron Dimethyl Sulfide complex (24.3 g) at 0-10° C. The reaction mass was stirred for 1-2 hr at 0-10° C. The progress of the reaction was monitored by HPLC. After the completion of the reaction, methanol (100 ml) was slowly added to the reaction mass for 30 minutes and stirred for 15 minutes at 0-10° C. The contents were distilled under vacuum at a temperature of 40-45° C. and cooled to 25-30° C. The cooled reaction mixture was slowly added to hydrochloric acid solution at 25-30° C. and stirred for 1-2 hours at the same temperature. The resulted solid was filtered, washed with water (300 ml) and dried at 65-70° C. for 8 hours. % Yield: 95%

Example 2: Preparation of Compound of Formula VI, Where A is TBDMS; and L is Bromo

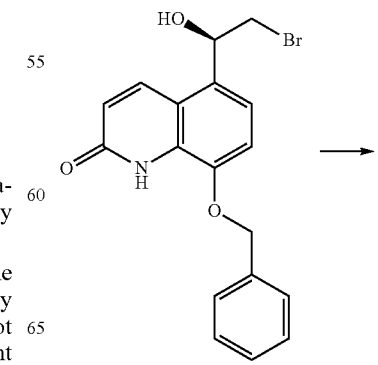

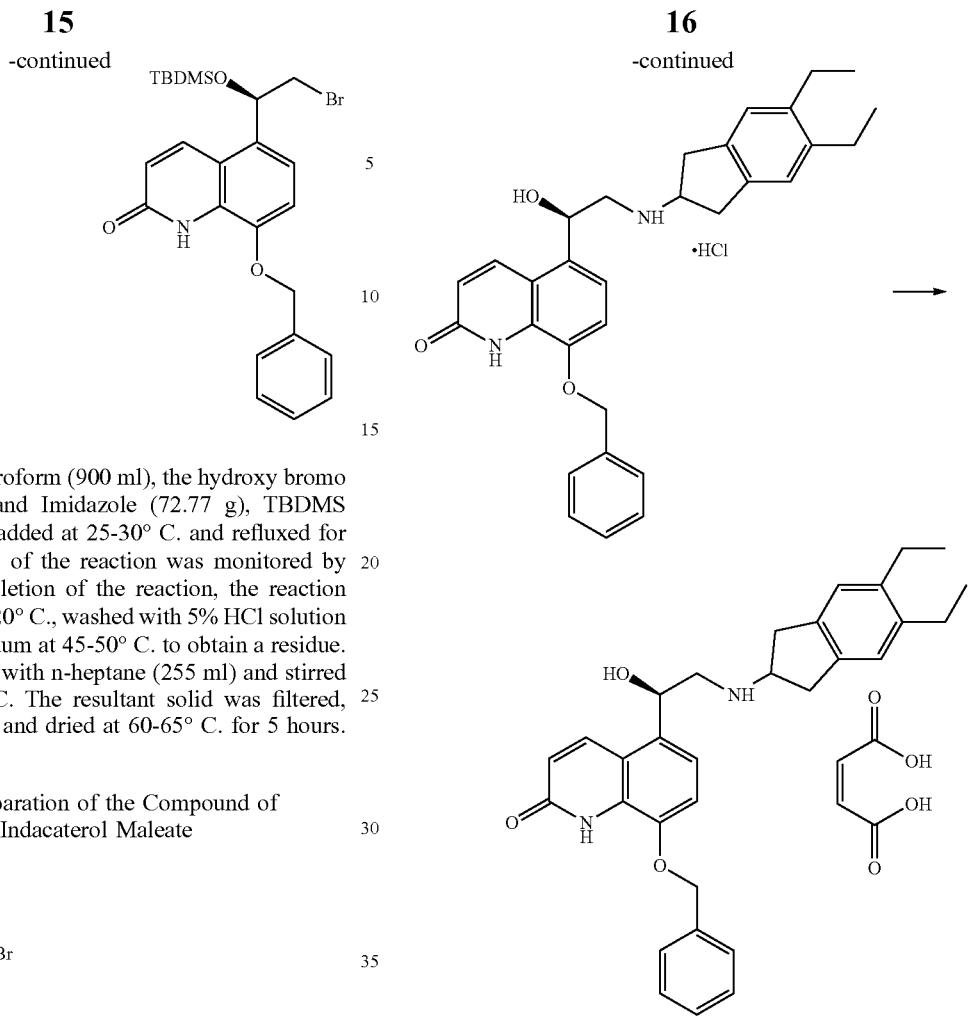

To a mixture of Chloroform (900 ml), the hydroxy bromo compound (100 gm) and Imidazole (72.77 g), TBDMS chloride solution were added at 25-30° C. and refluxed for 10 hours. The progress of the reaction was monitored by HPLC. After the completion of the reaction, the reaction mass was cooled to 15-20° C., washed with 5% HCl solution and distilled under vacuum at 45-50° C. to obtain a residue. The residue was mixed with n-heptane (255 ml) and stirred for 1 hour at 25-30° C. The resultant solid was filtered, washed with n-heptane and dried at 60-65° C. for 5 hours. Yield: 85%

Example-3: Preparation of the Compound of Benzyl Indacaterol Maleate

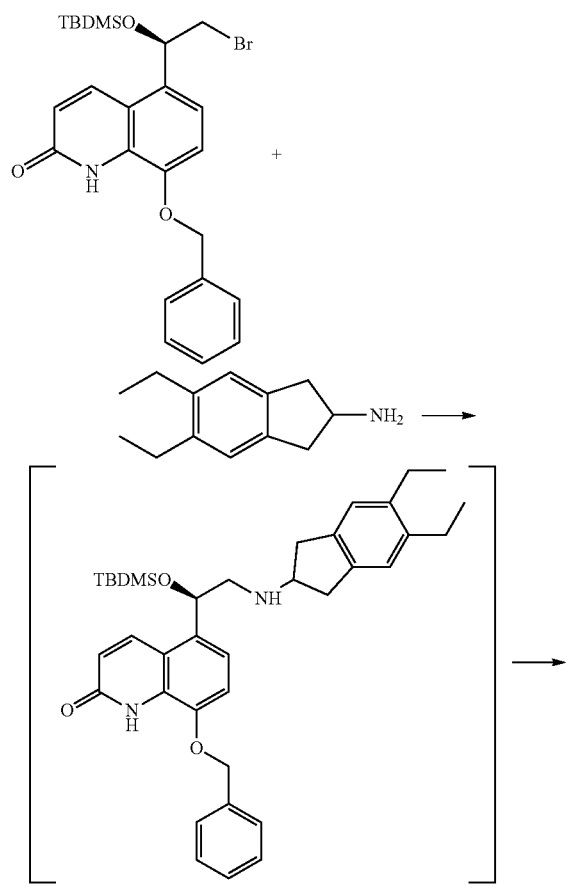

Step-A:

5,6-Diethyl-2-amino indane (87.14 g) was added to a mixture of 1-methyl pyrrolidone (500 ml) and silyl protected bromo compound (150 g) and heated to 95-100° C. The reaction mixture was maintained for 12 hours at 95-100° C. till the completion of the reaction. The progress of the reaction was monitored by HPLC. The reaction mixture was cooled to 25 to 30° C., followed by the addition of water (300 ml) and ethylacetate (500 ml). The organic layer thus separated and was distilled under vacuum at 50-55° C. to obtain a residue.

Step-B:

To the obtained residue in Tetrahydrofuran (500 ml), Tetra-n-butylammonium fluoride (58.05 g) was added and heated to 50-55° C. The reaction mixture was stirred for 6 hours at a temperature of 50-55° C. The progress of the reaction was monitored by HPLC. The reaction mixture was distilled under vacuum at 45-50° C. to get a residue. The obtained residue was dissolved in diluted hydrochloric acid (800 ml), stirred for 1 hour at a temperature of 25-30° C. The isolated solid was filtered, washed with water (100 ml) and dried at 60-65° C. for 8 hours. Yield: 78.22%

Step-C:

To the product obtained in the aforementioned step-B, water and dichloromethane was added and the pH was adjusted to 9.0-9.5 with sodium carbonate solution. The organic layer thus separated was distilled under vacuum at 40-45° C. to get a residue. The obtained residue was mixed with isopropyl alcohol (200 ml) and acetic acid (100 ml) and the contents was heated to 45-50° C. A isopropanolic solution of maleic acid (13.22 g of maleic acid in 100 of isopropanol) was slowly added to the contents at 45-50° C. and heated to 60-65° C. for 1 hour. The contents were than cooled to 25-30° C. and stirred for 2.0 hours at the same temperature. The resultant solid was filtered, washed with isopropyl alcohol (100 ml) and dried at 55-60° C. for 5 hours. Yield: 95%.

Example-4: Preparation of Indacaterol Free Base

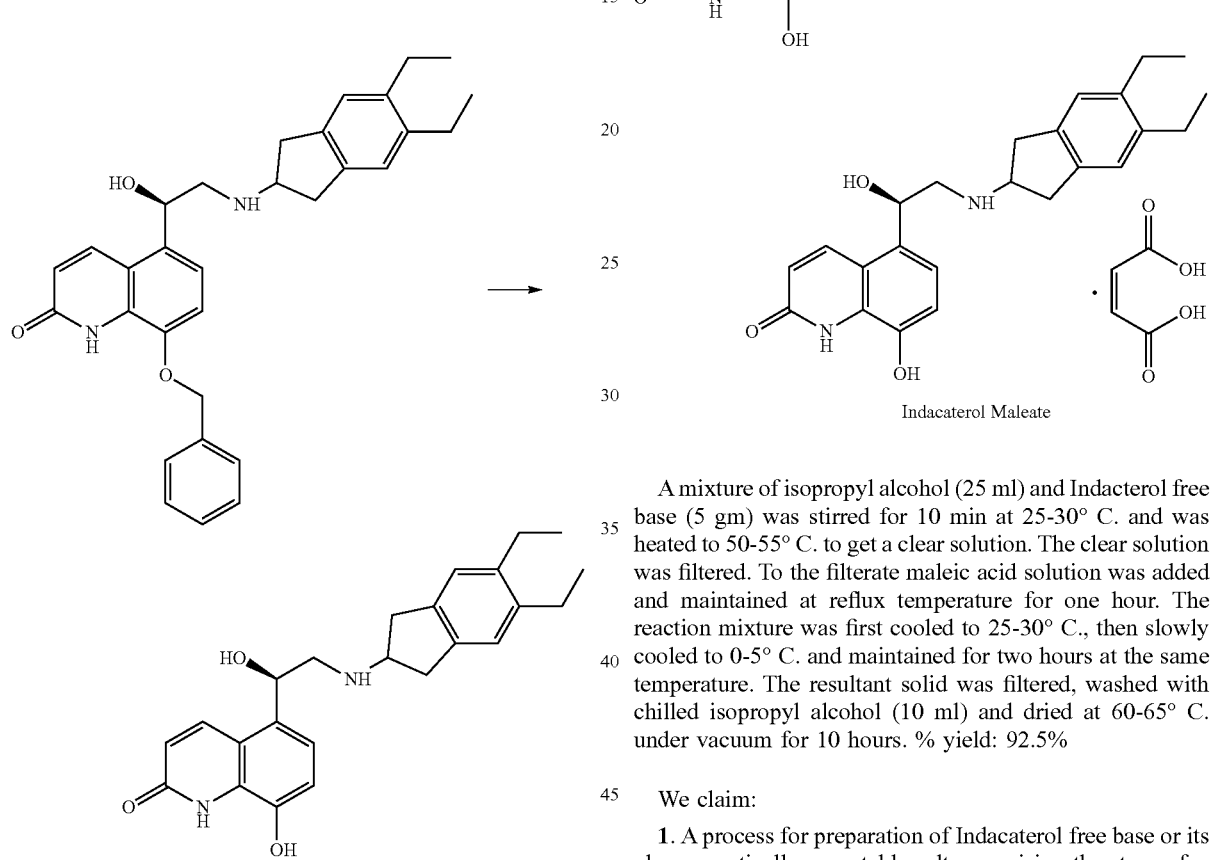

To a mixture of methanol (100 ml), acetic acid (10 ml), the benzyl indacaterol (10 g), palladium-Carbon (1.0 g) was added and then maintained for 4 hr at 25-30° C. with a hydrogen pressure of 3-4 Kg/cm². The progress of the reaction was monitored by HPLC. After completion of the reaction, the catalyst was filtered, washed with methanol (10 ml) and filtrate was distilled under vacuum at 50-55° C. to get a residue. The residue was mixed with dichloromethane and water. The separated dichloromethane layer was distilled under vacuum at 40-45° C. to get a residue. The residue thus obtained was dissolved in acetonitrile (30 ml) and cooled to 0-5° C. The contents were stirred for 1 hour at 0-5° C. till the formation of the solid. The formed solid was filtered, washed with acetonitrile (10 ml) and dried at 60-65° C. for 5 hours. % Yield: 88.5%

Example-5: Preparation of the Indacaterol Maleate

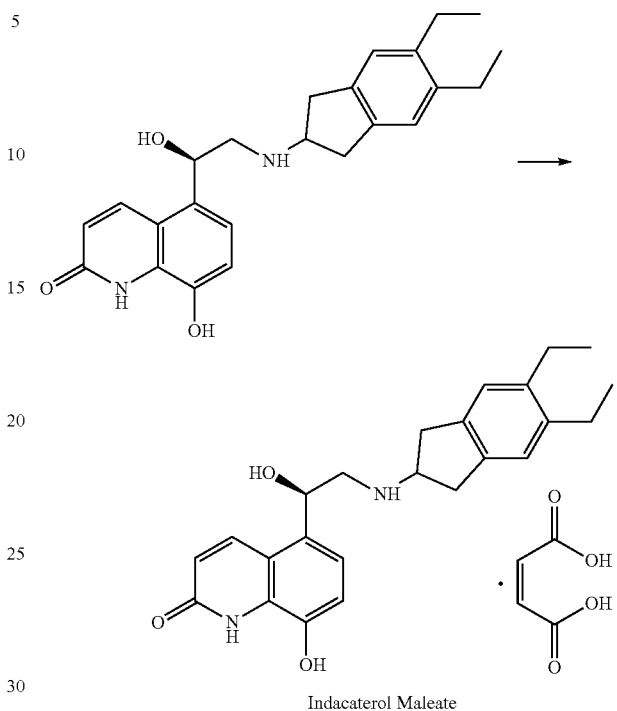

Indacaterol Maleate

A mixture of isopropyl alcohol (25 ml) and Indacterol free base (5 gm) was stirred for 10 min at 25-30° C. and was heated to 50-55° C. to get a clear solution. The clear solution was filtered. To the filterate maleic acid solution was added and maintained at reflux temperature for one hour. The reaction mixture was first cooled to 25-30° C., then slowly cooled to 0-5° C. and maintained for two hours at the same temperature. The resultant solid was filtered, washed with chilled isopropyl alcohol (10 ml) and dried at 60-65° C. under vacuum for 10 hours. % yield: 92.5%

We claim:

1. A process for preparation of Indacaterol free base or its pharmaceutically acceptable salt comprising the steps of:
   i) treating the compound of formula II

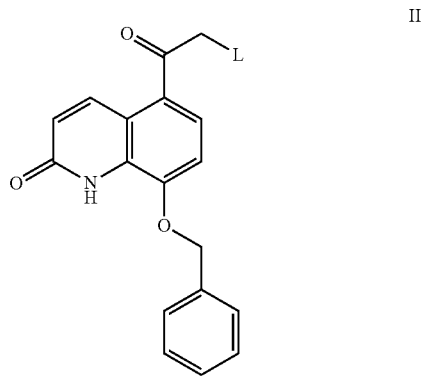

II with the reducing agent to obtain compound of formula III

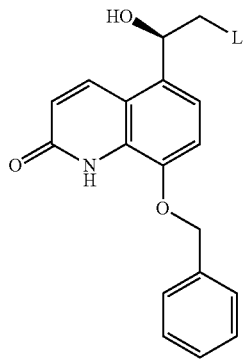

where L is good leaving group;

ii) treating compound of formula III with silylated protecting reagent to obtain compound of formula IV

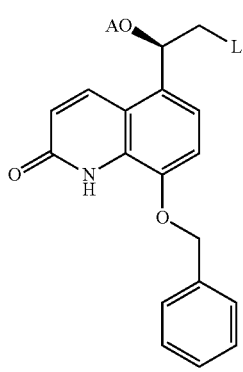

where A is silylated protective group;

iii) reacting the compound of formula IV with compound of formula V or its derivatives in the presence of a base

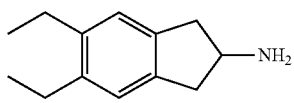

to obtain compound of formula VI,

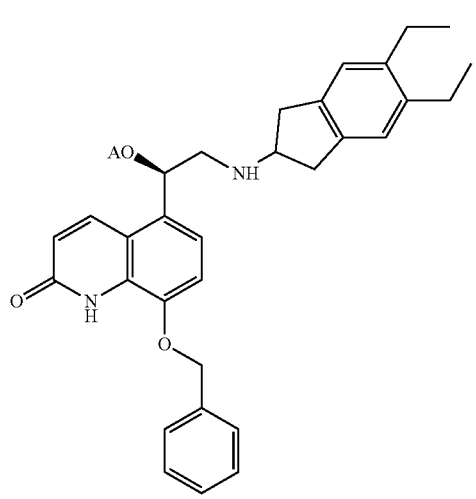

iv) desilylating compound of formula VI to obtain compound of formula VII

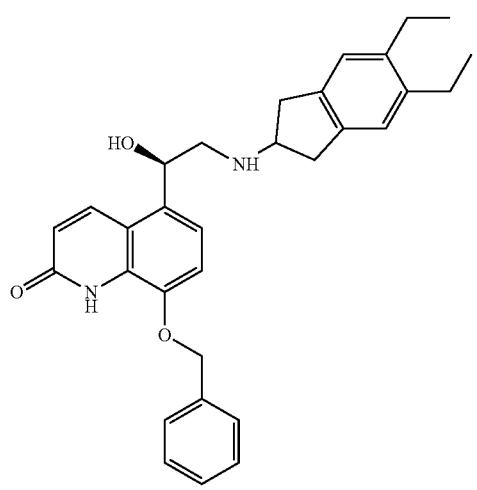

v) debenzylating the compound of formula VII to obtain compound of formula I Indacaterol free base

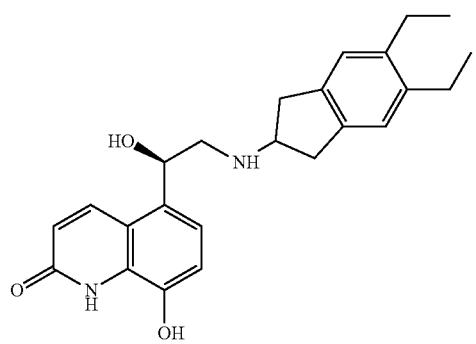

vi) optionally converting the compound of formula I into its pharmaceutically acceptable salts.

2. A process for the preparation of compound of formula VI

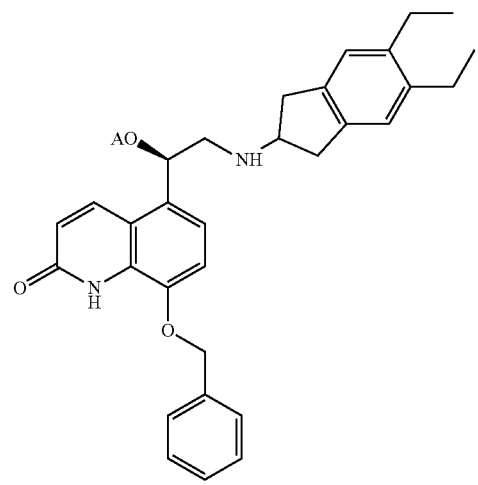

comprising the step of:
i) reacting the compound of formula IV

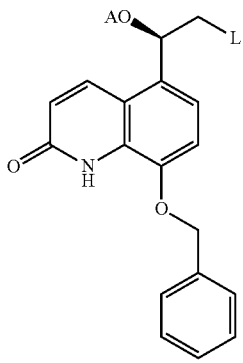

with compound of formula V or its derivatives in the presence of base,

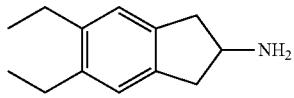

to obtain compound of formula VI, wherein A is silylated protective group.

3. The process as claimed in claim 1, wherein reducing agent used in step (i) is R-Methyl CBS.

4. The process as claimed in claim 1, wherein silylating agent used in step (ii) is tert-Butyldimethylsilyl chloride (TBDMSCl).

5. The process as claimed in claim 1, wherein base used in step (iii) is N-methyl pyrrolidone.

6. The process as claimed in claim 1, where in desilylating agent used in step (iv) is tetra-n-butylammonium fluoride.

7. The process as claimed in claim 1, where in debenzylating agent used in step (v) is palladium with carbon.

8. The process as claimed in claim 1, where in solvents used in step (i) to step (vi) are methanol, tetrahydrofuran, chloroform, ethyl acetate, methylene dichloride and isopropyl alcohol.

9. The process as claimed in claim 2, wherein base used in step (i) is N-methyl pyrrolidone.

10. The process as claimed in claim 2, wherein the reaction in step (i) takes place at a temperature between 95° C. to 100° C.

* * * * *